United States Patent
Heitmann et al.

(10) Patent No.: US 10,952,935 B2
(45) Date of Patent: Mar. 23, 2021

(54) COSMETIC PREPARATION CONTAINING SODA-LIME-BOROSILICATE GLASS BEADS

(71) Applicant: BEIERSDORF AG, Hamburg (DE)

(72) Inventors: Birgit Heitmann, Barsbuettel (DE); David Schlenker, Hamburg (DE); Andreas Bleckmann, Ahrensburg (DE)

(73) Assignee: BEIERSDORF AG, Hamburg (DE)

( * ) Notice: Subject to any disclaimer, the term of this patent is extended or adjusted under 35 U.S.C. 154(b) by 0 days.

(21) Appl. No.: 16/483,465

(22) PCT Filed: Jan. 30, 2018

(86) PCT No.: PCT/EP2018/052219
§ 371 (c)(1),
(2) Date: Aug. 5, 2019

(87) PCT Pub. No.: WO2018/145946
PCT Pub. Date: Aug. 16, 2018

(65) Prior Publication Data
US 2020/0009024 A1   Jan. 9, 2020

(30) Foreign Application Priority Data
Feb. 7, 2017 (DE) .......................... 102017201869.0

(51) Int. Cl.
*A61K 8/02* (2006.01)
*A61K 8/04* (2006.01)
*A61K 8/25* (2006.01)
*A61K 8/92* (2006.01)
*A61Q 17/04* (2006.01)

(52) U.S. Cl.
CPC .............. *A61K 8/0279* (2013.01); *A61K 8/04* (2013.01); *A61K 8/25* (2013.01); *A61K 8/92* (2013.01); *A61Q 17/04* (2013.01)

(58) Field of Classification Search
CPC .......... A61K 8/0279; A61K 8/04; A61K 8/25; A61K 8/92; A61K 17/04
See application file for complete search history.

(56) References Cited

U.S. PATENT DOCUMENTS

| | | |
|---|---|---|
| 4,944,937 A | 7/1990 | McCall |
| 2003/0228339 A1 | 12/2003 | El-Nokaly |
| 2005/0036961 A1 | 2/2005 | Hansenne |
| 2006/0115439 A1 | 6/2006 | Lu |
| 2011/0168200 A1 | 7/2011 | Bourdin |

FOREIGN PATENT DOCUMENTS

EP   1506772 A2   2/2005

OTHER PUBLICATIONS

Anonymous: "Product Information: 3M Glass Bubbles K series Series", Sep. 1, 2007 (Sep. 1, 2007), pp. 1-4.

*Primary Examiner* — Shirley V Gembeh
(74) *Attorney, Agent, or Firm* — Abel Schillinger, LLP

(57) ABSTRACT

Cosmetic preparation which contains at least one oil phase and glass beads of soda-lime-borosilicate.

20 Claims, No Drawings

COSMETIC PREPARATION CONTAINING SODA-LIME-BOROSILICATE GLASS BEADS

BACKGROUND OF THE INVENTION

1. Field of the Invention

The present invention relates to a cosmetic preparation comprising at least one oil phase and soda-lime-borosilicate glass beads.

2. Discussion of Background Information

The desire to look beautiful and attractive is naturally rooted in humans. Although ideals of beauty have changed over time, the pursuit of a flawless appearance has always been aimed for by humans. An essential part of a beautiful and attractive appearance is the condition and complexion of the skin.

In order for the skin to be able to perform the full range of its biological functions, it requires regular cleansing and care. Cleansing of the skin serves to remove dirt, sweat and residual dead skin particles, which form an ideal nutrient source for all kinds of germs and parasites. Skin cleansing is generally effected with the aid of surface-active preparations (soaps, surfactants, less frequently alcoholic preparations) which are in the form of foam-forming gels or solids (soap bars) and after application to the skin are rinsed off again with water.

Skin care products, generally creams, ointments or lotions, mostly serve for moisturizing and refatting the skin. Active ingredients are commonly added thereto, which are intended to regenerate the skin and for example to prevent and reduce the premature aging thereof (e.g. the appearance of fine lines and wrinkles).

The plethora of commercially available skin care products, which also include sunscreens, should not however obscure the fact that these preparations from the prior art have a series of disadvantages.

Cosmetic skin care products, even those based on an ethanolic solution, typically comprise oil components and other more or less sticky ingredients, which results in powdery, fine-grained particles that adhere more strongly to the skin. This problem is particularly bothersome in the case of sunscreens which are applied by consumers on the beach. The problem of so-called sand adhesion in the case of sunscreens has been described repeatedly in the literature. However, this problem also arises with other cosmetic products and other daily situations, for example in day or night creams in connection with house dust or pollen.

The object of the present invention, therefore, was to reduce particle adhesion to the skin caused by the cosmetic preparation and especially sand adhesion to the skin caused by cosmetics (particularly sunscreen compositions).

A possible solution to the problem according to the prior art consists of incorporating so-called powder raw materials composed of plastic particles that are solid at room temperature in the preparations. These plastic particles solid at room temperature consist of polyethylene, polypropylene, polymethyl methacrylate or nylon. This is also the definition according to the invention for these substances. The disadvantage now of this prior art is that the use of these substances is increasingly considered as undesirable in the context of the so-called "microplastic" discussion, i.e. the discussion around the use of plastic particles in cosmetics and the persistence thereof in the environment after application of cosmetics. Whether and potentially in which context this discussion is justified, may remain undecided in the context of this disclosure. The fact is, however, that there is an increasing interest among consumers in cosmetic products which no longer comprise these ingredients.

The object of the present invention, therefore, was to reduce particle adhesion to the skin caused by the cosmetic preparation and especially sand adhesion to the skin caused by cosmetics (particularly sunscreen compositions) without using plastic particles for this purpose that are solid at room temperature, i.e. polyethylene, polypropylene, polymethyl methacrylate or nylon.

SUMMARY OF THE INVENTION

Surprisingly, these objects are achieved by means of a cosmetic preparation containing at least one oil phase and soda-lime-borosilicate glass beads.

In this case, it is preferable in accordance with the invention if the preparation is free of plastic particles that are solid at room temperature.

Glass beads for cosmetic preparations are known, for example composed of alkali-lime glass (e.g. from GP Cosmetics) or magnesium silicate (e.g. Covabead Crystal from Sensient Cosmetic Technologies). However, these have the disadvantage that, in emulsions, i.e. the most widely used cosmetic preparation form, they lead to discolorations of the preparation. There are also stability problems with UV filters encapsulated with silica (e.g. Eusolex UV pearls from Merck). However, it was the object of the present invention to develop stable (particularly color-stable) preparations, especially emulsions (and here O/W emulsions).

It is advantageous in accordance with the invention if the glass beads according to the invention have a particle diameter of 5 to 120 μm.

The particle size (particle diameter) of the glass beads according to the invention can be determined in this case in accordance with customary standards, for example by sieves. Of course, it is known to those skilled in the art that the particle size (grain size) is always subject to a certain size distribution. The size specification therefore signifies that no larger glass beads are used than those having a particle diameter of 120 μm and it is not critical if minor amounts of smaller particles are present in the preparation as impurities (for example formed by "broken glass").

It is advantageous in accordance with the invention if the glass beads according to the invention are hollow.

Embodiments of the present invention that are advantageous according to the invention are characterized in that the density of the glass beads is 0.1 to 1.0 g/cubic centimeter. In this case, a density of 0.13 to 0.63 is preferred in accordance with the invention.

Moreover, it is advantageous in accordance with the invention if the glass beads have an oil absorption of 0.2 to 0.6 grams of oil per cubic centimeter of glass beads, measured in accordance with ASTM D281-95. In this case, an oil absorption of 0.3 to 0.5 grams of oil per cubic centimeter of glass beads, measured according to ASTM D281-95, is preferable in accordance with the invention.

In the context of the present invention, it is advantageous if the glass beads have a pH of 9 to 10, measured in accordance with ASTM D3100-1982.

It is advantageous in accordance with the invention if the glass beads have a softening temperature of 550 to 650° C. Here, the softening after 2 hours' storage at the appropriate temperature is determined. In accordance with the invention, preference is given to a softening temperature of 590 to 610° C., wherein it is ideally 600° C.

Also in accordance with the invention is the use of the glass beads according to the invention for reducing the adhesion of sand, pollen or dust to the skin caused by treating the skin with cosmetics, especially sunscreen compositions.

It is of advantage in accordance with the invention if the preparation comprises the glass beads in an amount of 0.1 to 10% by weight, based on the total weight of the preparation. In this case, a content from 1 to 6% by weight, based on the total weight of the preparation, is preferred in accordance with the invention.

Embodiments of the present invention that are advantageous according to the invention are characterized in that the oil phase of the preparation comprises one or more oil components selected from the group of compounds comprising diisopropyl adipate, caprylic/capric triglyceride (INCI Caprylic/Capric Triglycerides), isopropyl palmitate, dimethicone, cyclomethicone, octyldodecanol, ethylhexyl cocoate, myristyl myristate, hydrogenated coco-glycerides (INCI Hydrogenated Coco-Glycerides), dicaprylyl carbonate, C18-38 alkyl hydroxystearoryl stearate (INCI C18-38 Alkyl Hydroxystearoyl Stearate), di-n-butyl adipate, butylene glycol dicaprylate/dicaprate (INCI Butylene Glycol Dicaprylate/Dicaprate), C12-15 alkyl benzoate (INCI C12-15 Alkyl Benzoate), 2-phenylethyl benzoate (INCI Phenethyl Benzoate), di C12-13 alkyl tartrate (INCI Di-C12-13 Alkyl Tartrate), butylene glycol cocoate (INCI: Butylene Glycol Cocoate), dicaprylyl ether, isodecyl neopentanoate, tridecyl trimellitate, isopropyl stearate, C12.13 alkyl lactate, 2-propylheptyl octanoate, isopropyl lauryl sarcosinate. The oil components preferred in accordance with the invention are in this case diisopropyl adipate, caprylic/capric triglyceride (INCI Caprylic/Capric Triglycerides), octyldodecanol, ethylhexyl cocoate, myristyl myristate, hydrogenated coco-glycerides (INCI Hydrogenated Coco-Glycerides), di-n-butyl adipate, butylene glycol dicaprylate/dicaprate (INCI Butylene Glycol Dicaprylate/Dicaprate), C12-15 alkyl benzoate (INCI C12-15 Alkyl Benzoate), 2-phenylethyl benzoate (INCI Phenethyl Benzoate).

It is advantageous in accordance with the invention if the total amount of these oil components that are advantageous in accordance with the invention is from 1 to 20% by weight, based on the total weight of the preparation, the preferred amount range of which is from 2 to 15% by weight, based on the total weight of the preparation.

It is advantageous in accordance with the invention if the preparation according to the invention comprises one or more UV filters selected from the group of compounds phenylene-1,4-bis-(2-benzimidazyl)-3,3',-5,5'-tetrasulfonic acid salts; 2-phenylbenzimidazole-5-sulfonic acid salts; 1,4-di(2-oxo-10-sulfo-3-bornylidenemethyl)benzene and salts thereof; 4-(2-oxo-3-bornylidenemethyl)benzenesulfonic acid salts; 2-methyl-5-(2-oxo-3-bornylidenemethyl)sulfonic acid salts; 2-(2H-benzotriazol-2-yl)-4-methyl-6-[2-methyl-3-[1,3,3,3-tetramethyl-1-[(trimethylsilyl)oxy]disiloxanyl] propyl]phenol; 3-(4-methylbenzylidene)camphor; 3-benzylidenecamphor; ethylhexyl salicylate; terephthalidenedicamphorsulfonic acid; 2-ethylhexyl 4-(dimethylamino)benzoate; amyl 4-(dimethylamino)benzoate; di(2-ethylhexyl) 4-methoxybenzalmalonate; 2-ethylhexyl 4-methoxycinnamate; isoamyl 4-methoxycinnamate; 2-hydroxy-4-methoxybenzophenone, 2-hydroxy-4-methoxy-4'-methylbenzophenone; 2,2'-dihydroxy-4-methoxybenzophenone; hexyl 2-(4'-diethylamino-2'-hydroxybenzoyl) benzoate; 4-(tert-butyl)-4'-methoxydibenzoylmethane; homomenthyl salicylate; 2-ethylhexyl 2-hydroxybenzoate; 2-ethylhexyl 2-cyano-3,3-diphenylacrylate; dimethicodiethylbenzalmalonate; 2-ethylhexyl 2-cyano-3,3-diphenylacrylate; 3-(4-(2,2-bis ethoxycarbonylvinyl)-phenoxy)propenyl) methoxysiloxane/dimethylsiloxane-copolymer; dioctylbutylamidotriazone (INCI: Diethylhexyl Butamidotriazone); 2,4-bis[5-1(dimethylpropyl)benzoxazol-2-yl-(4-phenyl)imino]-6-(2-ethylhexyl)imino-1,3,5-triazine with (CAS No. 288254-16-0); tris(2-ethylhexyl) 4,4',4"-(1,3,5-triazine-2,4,6-triyltriimino)trisbenzoate (also: 2,4,6-tris[anilino-(p-carbo-2'-ethyl-1'-hexyloxy)]-1,3,5-triazine (INCI: Ethylhexyl Triazone); 2,4-bis{[4-(2-ethylhexyloxy)-2-hydroxy]phenyl}-6-(4-methoxyphenyl)-1,3,5-triazine; 4-dicyanomethylene-2,6-dimethyl-1,4-dihydropyridine N-(ethyloxysulfate ester salts), titanium dioxide; zinc oxide.

In this case, it is preferable in accordance with the invention if the preparation according to the invention is free of 2-ethylhexyl 2-cyano-3,3-diphenylacrylate, 2-hydroxy-4-methoxybenzophenone, 2-ethyl hexyl 4-methoxycinnamate, isoamyl 4-methoxycinnamate and/or 3-(4-methylbenzylidene)camphor. Particularly preferably in this case, the use of 2-ethylhexyl 4-methoxycinnamate, isoamyl 4-methoxycinnamate, 3-(4-methylbenzylidene)-camphor and 2-hydroxy-4-methoxybenzophenone should be avoided.

In contrast, particular preference in accordance with the invention is given to the use of 4-(tert-butyl)-4'-methoxydibenzoylmethane; hexyl 2-(4'-diethylamino-2'-hydroxybenzoyl)benzoate (INCI: Diethylamino Hydroxybenzoyl Hexyl Benzoate), 2-phenylbenzimidazole-5-sulfonic acid salts, ethylhexyl salicylate; dioctylbutylamidotriazone (INCI: Diethylhexyl Butamidotriazone), tris(2-ethylhexyl) 4,4',4"-(1,3,5-triazine-2,4,6-triyltriimino)trisbenzoate (also: 2,4,6-tris[anilino-(p-carbo-2'-ethyl-1'-hexyloxy)]-1,3,5-triazine (INCI: Ethylhexyl Triazone) and 2,4-bis{[4-(2-ethylhexyloxy)-2-hydroxy]phenyl}-6-(4-methoxyphenyl)-1,3,5-triazine, wherein these UV filters can be used singly or as a mixture.

Embodiments of the present invention that are advantageous according to the invention are also characterized in that the preparation is in the form of an emulsion. In this case, O/W emulsions (oil-in-water emulsions) are preferred in accordance with the invention.

In such a case, it is particularly advantageous in accordance with the invention if the preparation is in the form of an O/W emulsion, which has been emulsified with one or more emulsifiers selected from the group of the compounds glyceryl stearate citrate, glyceryl stearate (self-emulsifying), stearic acid, stearate salts, polyglyceryl-3 methylglycose distearate, sodium stearoyl glutamate, sodium cetearyl sulfate, potassium cetyl phosphate, cetearyl sulfosuccinate, polyglyceryl-10 stearate, polyglyceryl-10 laurate, polyglyceryl-10 caprate. These emulsifiers are typically used at a total concentration of 0.5 to 10% by weight, based on the total weight of the preparation.

In the context of the present invention, it is advantageous if the preparation contains one or more alcohols selected from the group of the compounds ethanol, glycerol, ethylhexylglycerin, phenoxyethanol, polyglyceryl-2 caprate, propylene glycol, butylene glycol, 2-methylpropane-1,3-diol, 1,2-pentanediol, 1,2-hexanediol, 1,2-octanediol, 1,2-decanediol.

These emulsifiers may be used at a total concentration of 0.2 to 80% by weight, based on the total weight of the preparation.

Embodiments of the present invention that are advantageous according to the invention are characterized in that the preparation contains one or more compounds selected from the group of the compounds alpha-lipoic acid, folic acid, phytoene, D-biotin, coenzyme Q10, alpha-glucosylrutin, carnitine, carnosine, isoflavonoids, flavonoids, creatine, creatinine, taurine, β-alanine, panthenol, polidocanol, tocopheryl acetate, dihydroxyacetone, glycerylglucose, (2-hydroxyethyl)urea, vitamin E and vitamin E acetate, hyaluronic acid and/or sodium salts thereof, menthol, gylcyrrhetic acid and/or licochalcone A.

Last but not least, it is advantageous in accordance with the invention if the preparation contains one or more polymers selected from the group of the compounds xanthan gum, tapioca starch, hydroxyethylcellulose, carbomer, acrylate/C10-30 alkyl acrylate, vinylpyrrolidone/hexadecene copolymer.

In addition, the cosmetic preparation can be composed of such cosmetics customary for such cases and may comprise the appropriate known ingredients.

Comparative Experiment

The following formulations were prepared and the sand adhesion was determined by the following method.

| INCI | sweat 249 | _sweat_260 | _sweat_261 |
|---|---|---|---|
| Glass beads of largest diameter ca. 150 μm (e.g. 3M Glass Bubbles K15) | 0 | 5 | 0 |
| Glass beads of largest diameter ca. 30 μm (e.g. 3M GLASS BUBBLES IM30K) | 0 | 0 | 5 |
| Tocopheryl Acetate | 0.11 | 0.11 | 0.11 |
| Menthol | 0.05 | 0.05 | 0.05 |
| C12-15 Alkyl Benzoate | 5 | 5 | 5 |
| Diisopropyl Adipate | 3 | 3 | 3 |
| Butylene Glycol Dicaprylate/Dicaprate | 4 | 4 | 4 |
| Polyglyceryl-3 Methylglucose Distearate | 0.2 | 0.2 | 0.2 |
| Silica Dimethyl Silylate | 1 | 1 | 1 |
| Tapioca Starch + Aqua | 4 | 4 | 4 |
| Perfume | 0.4 | 0.4 | 0.4 |
| Glycerin + Aqua | 1 | 1 | 1 |
| Aqua + Sodium Hydroxide | 0.623 | 0.623 | 0.623 |
| Phenoxyethanol | 0.5 | 0.5 | 0.5 |
| Hydroxyethylcellulose | 0.1 | 0.1 | 0.1 |
| Carbomer | 0.125 | 0.125 | 0.125 |
| Acrylates/C10-30 Alkyl Acrylate Crosspolymer | 0.2 | 0.2 | 0.2 |
| Xanthan Gum | 0.2 | 0.2 | 0.2 |
| Aqua | to 100 | to 100 | to 100 |
| Alcohol Denat. + Aqua | 10 | 10 | 10 |
| Aqua + Trisodium EDTA | 1 | 1 | 1 |
| Ethylhexyl Salicylate | 5 | 5 | 5 |
| Bis-Ethylhexyloxyphenol Methoxyphenyl Triazine | 4 | 4 | 4 |
| Ethylhexyl Triazone | 3 | 3 | 3 |
| Butyl Methoxydibenzoylmethane | 4.75 | 4.75 | 4.75 |
| Phenylbenzimidazole Sulfonic Acid | 1 | 1 | 1 |

In vitro Sand Adhesion 50 mg of the test emulsions were applied to PMMA Schönberg plaques (5.0×5.0 cm) and spread uniformly over the plaque, using a fingerstall. The example formulation applied is then dried at room temperature for 15 minutes. After this time, the weight of the dried plaques was determined using an analytical balance. Subsequently, the plaques were sprinkled with fine sea sand in excess (1.07711.1000 extra pure sea sand, Merck KGaA). Loosely adhering sand was removed using reproducible uniform force by causing the plaques to slide once along a slide apparatus (see below) intended for that purpose.

The adhering sand remaining on the plaque thereafter was determined by reweighing. The sand adhesion can be determined using the following equation:

$$\Delta(\text{Adhesion})[\text{mg}]=m(\text{plaque with sand})[\text{mg}]-m(\text{plaque with cream applied})[\text{mg}]$$

The slide apparatus is a construction in the form of a triangle on which the width of the slide is 5 cm. The construction of the slide apparatus takes the form of a right-angled triangle for which the width of the slide is 5 cm. The adjacent side of the right-angled triangle (=the standing surface of the slide) has a length of 13.5 cm; the opposite side (=drop height) has a length of 49 cm. The hypotenuse, on which the sliding takes place, and the standing surface enclose an angle of 275°.

The experiments were repeated 10× per formulation and the corresponding mean was calculated.

Individual Data for Sand Adhesion:

| Sample | w Plaque in g | w Plaque + sand in g | w Sand absolute in g | Mean | Standard deviation |
|---|---|---|---|---|---|
| SWEAT: 249 a-15 | 7.292 | 7.35 | 0.058 | | |
| SWEAT: 249 b-15 | 7.297 | 7.423 | 0.126 | | |
| SWEAT: 249 c-15 | 7.299 | 7.429 | 0.13 | | |
| SWEAT: 249 d-15 | 7.27 | 7.376 | 0.106 | | |
| SWEAT: 249 e-15 | 7.311 | 7.395 | 0.084 | | |
| SWEAT: 249 f-15 | 7.279 | 7.385 | 0.106 | | |
| SWEAT: 249 g-15 | 7.169 | 7.287 | 0.118 | | |
| SWEAT: 249 h-15 | 7.301 | 7.35 | 0.049 | | |
| SWEAT: 249 i-15 | 7.305 | 7.434 | 0.129 | | |
| SWEAT: 249 j-15 | 7.29 | 7.396 | 0.106 | 0.101 | 0.029 |
| SWEAT: 260 a-15 | 7.292 | 7.294 | 0.002 | | |
| SWEAT: 260 b-15 | 7.311 | 7.314 | 0.003 | | |
| SWEAT: 260 c-15 | 7.216 | 7.218 | 0.002 | | |
| SWEAT: 260 d-15 | 7.152 | 7.154 | 0.002 | | |
| SWEAT: 260 e-15 | 7.106 | 7.11 | 0.004 | | |
| SWEAT: 260 f-15 | 7.285 | 7.287 | 0.002 | | |
| SWEAT: 260 g-15 | 7.172 | 7.179 | 0.007 | | |
| SWEAT: 260 h-15 | 7.166 | 7.17 | 0.004 | | |
| SWEAT: 260 i-15 | 7.199 | 7.207 | 0.008 | | |
| SWEAT: 260 j-15 | 7.323 | 7.329 | 0.006 | 0.004 | 0.002 |
| SWEAT: 261 a-15 | 7.264 | 7.301 | 0.037 | | |
| SWEAT: 261 b-15 | 7.249 | 7.252 | 0.003 | | |
| SWEAT: 261 c-15 | 7.313 | 7.322 | 0.009 | | 0 |
| SWEAT: 261 d-15 | 7.323 | 7.327 | 0.004 | | |
| SWEAT: 261 e-15 | 7.298 | 7.318 | 0.02 | | |
| SWEAT: 261 f-15 | 7.307 | 7.317 | 0.01 | | |
| SWEAT: 261 g-15 | 7.325 | 7.332 | 0.007 | | |
| SWEAT: 261 h-15 | 7.291 | 7.299 | 0.008 | | |
| SWEAT: 261 i-15 | 7.291 | 7.295 | 0.004 | | |
| SWEAT: 261 j-15 | 7.325 | 7.331 | 0.006 | 0.011 | 0.010 |

| Sample | Adhering sand in mg/cm$^2$ (15 minutes) | Standard deviation |
|---|---|---|
| SWEAT: 249 N-free | 4.0 | 1.16 |
| SWEAT: 260 N-free + 5% 3M Glass Bubbles K15 | 0.2 | 0.08 |
| SWEAT: 261 N-free + 5% 3M Glass Bubbles IM30K | 0.4 | 0.4 |

DETAILED DESCRIPTION OF EMBODIMENTS OF THE INVENTION

Examples

The examples below are intended to illustrate the present invention without limiting it. Unless otherwise stated, all quantitative data, fractions and percentages are based on the weight and the total amount or on the total weight of the preparations.

|  | Examples | | | | | | | | | |
|---|---|---|---|---|---|---|---|---|---|---|
| INCI | 1 m [%] | 2 m [%] | 3 m [%] | 4 m [%] | 5 m [%] | 6 m [%] | 7 m [%] | 8 m [%] | 9 m [%] | 10 m [%] |
| Glass beads of largest diameter ca. 30 μm (e.g. 3M GLASS BUBBLES IM30K) | 2.5 | 5 | | | 2 | 6 | | | 3 | |
| Glass beads of largest diameter ca. 150 μm (e.g. 3M Glass Bubbles K15) | | | 2.5 | 5 | | | 2 | 6 | | 3 |
| VP/Hexadecene Copolymer | 0.5 | 1 | | 0.5 | | 1 | | 0.5 | | |
| Tocopheryl acetate | 0.06 | 0.1 | 0.01 | 0.15 | 0.06 | 0.5 | 0.1 | 0.06 | 0.15 | 0.1 |
| Panthenol | 1 | 1.4 | | 0.5 | 0.5 | | 1 | 1 | | 0.5 |
| Ethylhexylglycerol | 0.3 | 0.5 | 0.25 | | | | 0.3 | | | 0.25 |
| 1,2-Hexanediols | | | | 0.4 | | 1 | | | 1 | |
| Methylpropanediols | | | | | 0.2 | | | 0.2 | | |
| C12-15 Alkylbenzoate | 4.5 | 6 | 3 | | | 6 | 7 | | 7.5 | |
| Caprylic/Capric Triglycerides | | 4 | | | 2 | | | | 3 | |
| Isopropyl Palmitate | | | 4 | | | | | 3 | | 3 |
| Dimethicone | | | | 2 | 1 | | | 0.5 | | |
| Octyldodecanol | | | | 2 | | | | | 2 | |
| Ethylhexyl Cocoate | | | | | | 1 | | | 2 | 3 |
| Myristyl Myristate | 2 | 1 | 1.5 | | | 1 | | | | |
| Cetearyl Alcohol | | | | 1 | | | 1.5 | | | 1 |
| Hydrogenated Coco-Glycerides | | | | | 5 | | | 2 | | 1 |
| Butylene Glycol Dicaprylate/Dicaprate | 1 | | 3 | 1.5 | | | 2 | | | |
| Dicaprylyl Carbonate | 1 | | | 3 | | 3 | | | 1.5 | |
| C18-38 Alkyl Hydroxystearoyl Stearate | | | | | 0.5 | | | | | |
| Polyglyceryl-3 Methylglucose Distearate | | | | 0.15 | | | | | 0.15 | |
| Glyceryl Stearate Citrate | 2 | 3 | | | | 2 | | 2 | | |
| Glyceryl Stearate | | | 1 | | 1 | | | | | |
| Sodium Stearoyl Glutamate | | | | | | | | 0.5 | | |
| Glyceryl Stearate SE | | | | | | | 1 | | | 1 |
| Sodium Cetearal Sulfate | | | 0.15 | | 0.15 | | | | | 0.15 |
| Silica dimethyl Silylate | | 0.5 | 0.5 | | 0.3 | 1 | 0.5 | | 1 | |
| Tapioca starch | | | | | | | 3 | 3 | | |
| Perfume | 0.4 | 0.3 | 0.2 | 0.4 | | 0.4 | 0.5 | | 0.3 | 0.2 |
| Glycerol | 6 | 8 | 5 | 1 | 1 | 5 | 8 | 6 | 5 | 1 |
| Citric Acid | 0.07 | 0.09 | | | | 0.01 | | 0.008 | | |
| Sodium Citrate | 0.16 | 0.15 | | | | 0.16 | | 0.17 | | |
| Sodium Hydroxide | 0.05 | 0.08 | 0.07 | 0.08 | 0.05 | 0.03 | | 0.07 | 0.06 | 0.03 |
| Phenoxyethanol | 0.3 | 0.5 | 0.3 | 0.4 | 0.5 | 0.2 | | 0.5 | 0.3 | 0.4 |
| Methylparaben | 0.2 | 0.3 | 0.2 | 0.2 | 0.3 | | | 0.4 | 0.2 | 0.3 |
| Ethylparaben | 0.2 | 0.3 | 0.2 | 0.3 | | | | 0.2 | | 0.3 |
| Stearyl Alcohol | 0.8 | 0.8 | | | 1 | | 0.8 | 1.5 | | |
| Acrylates/C10-30Alkyl Acrylates Crosspolymer | 0.1 | 0.15 | 0.05 | | 0.2 | 0.1 | | 0.05 | 0.15 | 0.2 |
| Carbomer | | | | | 0.15 | | | | | |
| Hydroxyethylcellulose | | | | | 0.1 | | | | | |
| Xanthan Gum | 0.3 | 0.2 | 0.5 | 0.4 | | 0.3 | 0.4 | 0.2 | 0.3 | 0.3 |
| Cetyl Alcohol | 0.5 | 1 | | | | | | | 2 | |
| Alcohol Denat | 4 | 6 | 4 | 8 | 10 | 4 | 6 | 6 | 8 | 10 |
| Trisodium EDTA | 1 | 0.5 | 1 | 1 | 1 | 0.5 | 0.5 | 1 | 1 | 1 |
| Homosalate | 9 | | 9 | 9 | 9.5 | 9 | 9 | 9 | 9 | 9 |
| Octocrylene | 9 | 9 | | | 9.5 | | | 8 | 8 | |
| Ethylhexyl Salicylate | 4.5 | | 4.75 | 4.75 | 4.75 | 4.75 | 4.75 | 4.75 | 4.75 | 4.75 |
| Butyl Methoxydibenzoylmethane | 4.5 | 4.5 | | 4.75 | 4.75 | 4.75 | 4.5 | 4.5 | 4.75 | 4.75 |
| Titanium dioxide | 3 | 6 | | | | | 1 | | 3.5 | |
| Bis-Ethylhexyloxyphenol Methoxyphenyl Triazine | | 3 | 4 | 4 | 3.5 | 4 | 4 | 3.5 | 3 | 4 |
| Ethylhexyl Triazone | | | 3 | 3 | | 3 | 3 | | | 3 |
| Diethylamino Hydroxybenzoyl Hexylbenzoate | | | 8 | | | | | | | |
| Polysilicone-15 | | 1 | | | | | | | | |
| Phenylbenzimidazole Sulfonic Acid | | | 1 | 1 | 1 | 1 | | 1.5 | 1.5 | 1 |
| Water | to 100 | to 100 | to 100 | to 100 | to 100 | to 100 | to 100 | to 100 | to 100 | to 100 |

What is claimed is:

1. A cosmetic preparation, wherein the preparation comprises at least one oil phase and soda-lime-borosilicate glass beads which have at least one of the following properties:
   (i) a density of from 0.13 g/cm$^3$ to 0.63 g/cm$^3$;
   (ii) an oil absorption, measured in accordance with ASTM D281-95, of from 0.2 to 0.6 grams of oil per cm$^3$ of glass beads;
   (iii) a pH of 9 to 10, measured in accordance with ASTM D3100-1982;
   (iv) a softening temperature of from 550° C. to 650° C.

2. The preparation of claim 1, wherein the glass beads are present in a concentration of from 0.1% to 10% by weight, based on a total weight of the preparation.

3. The preparation of claim 2, wherein the glass beads are present in a concentration of from 1% to 6% by weight.

4. The preparation of claim 1, wherein the preparation is free of plastic particles which are solid at room temperature.

5. The preparation of claim 1, wherein the glass beads have a particle diameter of from 5 µm to 120 µm.

6. The preparation of claim 1, wherein the glass beads are hollow.

7. The preparation of claim 1, wherein the glass beads have a density of from 0.1 g/cm$^3$ to 1.0 g/cm$^3$.

8. The preparation of claim 7, wherein the glass beads have a density of from 0.13 g/cm$^3$ to 0.63 g/cm$^3$.

9. The preparation of claim 8, wherein the glass beads have an oil absorption, measured in accordance with ASTM D281-95, of from 0.3 to 0.5 grams of oil per cm$^3$ of glass beads.

10. The preparation of claim 9, wherein the glass beads have a softening temperature of from 590° C. to 610° C.

11. The preparation of claim 1, wherein the glass beads have an oil absorption, measured in accordance with ASTM D281-95, of from 0.2 to 0.6 grams of oil per cm$^3$ of glass beads.

12. The preparation of claim 1, wherein the glass beads have a pH of 9 to 10, measured in accordance with ASTM D3100-1982.

13. The preparation of claim 1, wherein the glass beads have a softening temperature of from 550° C. to 650° C.

14. The preparation of claim 1, wherein the at least one oil phase comprises one or more oil components selected from diisopropyl adipate, caprylic/capric triglyceride, isopropyl palmitate, dimethicone, cyclomethicone, octyldodecanol, ethylhexyl cocoate, myristyl myristate, hydrogenated cocoglycerides, dicaprylyl carbonate, C18-38 alkyl hydroxystearoryl stearate, di-n-butyl adipate, butylene glycol dicaprylate/dicaprate, C12-15 alkyl benzoate, 2-phenylethyl benzoate, di C12-13 alkyl tartrate, butylene glycol cocoate, dicaprylyl ether, isodecyl neopentanoate, tridecyl trimellitate, isopropyl stearate, C12-13 alkyl lactate, 2-propylheptyl octanoate, isopropyl lauryl sarcosinate.

15. The preparation of claim 1, wherein the preparation further comprises one or more UV filters selected from phenylene-1,4-bis-(2-benzimidazyl)-3,3'-5,5'-tetrasulfonic acid salts; 2-phenylbenzimidazole-5-sulfonic acid salts; 1,4-di(2-oxo-10-sulfo-3-bornylidenemethyl)benzene and salts thereof; 4-(2-oxo-3-bornylidenemethyl)benzenesulfonic acid salts; 2-methyl-5-(2-oxo-3-bornylidenemethyl)sulfonic acid salts; 2-(2H-benzotriazol-2-yl)-4-methyl-6-[2-methyl-3-[1,3,3,3-tetramethyl-1-[(trimethylsilyl)oxy]disiloxanyl] propyl]phenol; 3-(4-methylbenzylidene)camphor; 3-benzylidenecamphor; ethylhexyl salicylate; terephthalidenedicamphorsulfonic acid; 2-ethylhexyl 4-(dimethylamino)benzoate; amyl 4-(dimethylamino)benzoate; di(2-ethylhexyl) 4-methoxybenzalmalonate; 2-ethylhexyl 4-methoxycinnamate; isoamyl 4-methoxycinnamate; 2-hydroxy-4-methoxybenzophenone, 2-hydroxy-4-methoxy-4'-methylbenzophenone; 2,2'-dihydroxy-4-methoxybenzophenone; hexyl 2-(4'-diethylamino-2'-hydroxybenzoyl) benzoate; 4-(tert-butyl)-4'-methoxydibenzoylmethane; homomenthyl salicylate; 2-ethylhexyl 2-hydroxybenzoate; 2-ethylhexyl 2-cyano-3,3-diphenylacrylate; dimethicodiethylbenzalmalonate; 2-ethylhexyl 2-cyano-3,3-diphenylacrylate; 3-(4-(2,2-bis ethoxycarbonylvinyl)phenoxy)propenyl)-methoxysiloxane/dimethylsiloxane-copolymer; dioctylbutylamidotriazone; 2,4-bis[5-1(dimethylpropyl) benzoxazol-2-yl-(4-phenyl)imino]-6-(2-ethylhexyl)imino-1,3,5-triazine; tris(2-ethylhexyl) 4,4',4"-(1,3,5-triazine-2,4,6-triyltriimino)trisbenzoate (also: 2,4,6-tris[anilino-(p-carbo-2'-ethyl-1'-hexyloxy)]-1,3,5-triazine); 2,4-bis{[4-(2-ethylhexyloxy)-2-hydroxy]phenyl}-6-(4-methoxyphenyl)-1,3,5-triazine; 4-dicyano-methylene-2,6-dimethyl-1,4-dihydropyridine N-(ethyloxysulfate ester salts); titanium dioxide; zinc oxide.

16. The preparation of claim 1, wherein the preparation is present as an emulsion.

17. The preparation of claim 1, wherein the preparation is present as an O/W emulsion emulsified with one or more emulsifiers selected from glyceryl stearate citrate, glyceryl stearate (self-emulsifying), stearic acid, stearate salts, polyglyceryl-3 methylglucose distearate, sodium stearoyl glutamate, sodium cetearyl sulfate, potassium cetyl phosphate, cetearyl sulfosuccinate, polyglyceryl-10 stearate, polyglyceryl-10 laurate, polyglyceryl-10 caprate.

18. The preparation of claim 1, wherein the preparation further comprises one or more alcohols selected from ethanol, glycerol, ethylhexylglycerin, phenoxyethanol, polyglyceryl-2 caprate, propylene glycol, butylene glycol, 2-methylpropane-1,3-diol, 1,2-pentanediol, 1,2-hexanediol, 1,2-octanediol, 1,2-decanediol.

19. The preparation of claim 1, wherein the preparation reduces particle adhesion to skin caused by the cosmetic preparation without glass beads.

20. A cosmetic preparation, wherein the preparation comprises at least one oil phase and soda-lime-borosilicate glass beads which have the following properties:
   (i) a density of from 0.13 g/cm$^3$ to 0.63 g/cm$^3$;
   (ii) an oil absorption, measured in accordance with ASTM D281-95, of from 0.3 to 0.5 grams of oil per cm$^3$ of glass beads;
   (iii) a pH of 9 to 10, measured in accordance with ASTM D3100-1982;
   (iv) a softening temperature of from 590° C. to 610° C.;
   and wherein the preparation reduces particle adhesion to skin caused by the cosmetic preparation without glass beads.

* * * * *